United States Patent [19]

Brunnmueller et al.

[11] Patent Number: 4,543,215

[45] Date of Patent: Sep. 24, 1985

[54] α-IMINODIACETONITRILES AND THEIR PREPARATION

[75] Inventors: Fritz Brunnmueller, Limburgerhof; Michael Kroener, Mannheim, both of Fed. Rep. of Germany

[73] Assignee: BASF Aktiengesellschaft, Ludwigshafen, Fed. Rep. of Germany

[21] Appl. No.: 547,851

[22] Filed: Nov. 2, 1983

[30] Foreign Application Priority Data

Nov. 15, 1982 [DE] Fed. Rep. of Germany ....... 3242193

[51] Int. Cl.⁴ .................. C07C 121/42; C07C 121/78
[52] U.S. Cl. ............................ 260/465.5 R; 260/464; 260/465 E
[58] Field of Search ................... 260/465 E, 465.5 R, 260/464

[56] References Cited

FOREIGN PATENT DOCUMENTS 1493752 11/1969 Fed. Rep. of Germany .
6321070 10/1983 Japan .

OTHER PUBLICATIONS

Berichte, 14 (1881), 1867–1870.
Annalen, 219 (1883), 186–194.
Annalen, 278 (1894), 229–233.
Bejaud et al., Bull. Soc. Chem. France 1976, 1425–1430.
J. Prakt. Chem. 89 (1914), 361–371.
Annalen, 177 (1875), 116–139.
Berichte, 13 (1880), 905–908.
Annalen, 200 (1880), 126–127.

*Primary Examiner*—Dolph H. Torrence
*Attorney, Agent, or Firm*—John H. Shurtleff

[57] ABSTRACT

Novel α-iminodiacetonitriles are prepared by a process in which an aldehyde-cyanohydrin or a haloacetonitrile is reacted with an aminonitrile, the reaction being carried out in the presence of a lower alkanol in the case of the preparation of symmetric α-iminodiacetonitriles, and in the presence of an auxiliary base in the case of the preparation employing a haloacetonitrile. The α-iminodiacetonitriles obtainable by the process of the invention are useful starting materials for the preparation of dyes, fungicides, bactericides, herbicides, textile assistants, anticorrosion agents, complex-forming agents, stabilizers in electroplating baths and inhibitors for antifreezes.

15 Claims, No Drawings

α-IMINODIACETONITRILES AND THEIR PREPARATION

The present invention relates to novel α-iminodiacetonitriles and processes for their preparation by reacting an aldehyde-cyanohydrin or a haloacetonitrile with an aminonitrile, the preparation of symmetric α-iminodiacetonitriles being carried out in the presence of a lower alkanol, and the preparation using a haloacetonitrile being carried out in the presence of an auxiliary base.

Annalen 177 (1875), 116–139 discloses that α-iminodicaprylonitrile

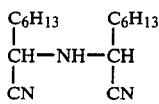

can be prepared by reacting enanthaldehyde/ammonia with hydrocyanic acid at 15°–47° C. and treating the reaction product with hydrochloric acid. In a similar manner, it is also possible to obtain α-iminodiisovaleronitrile ($R^1$, $R^2$=isopropyl; Ber. 13 (1880), 905–908), α-iminodipropionitrile ($R^1$, $R^2$=methyl; Annalen 200 (1880), 126–127), α-iminodiisocapronitrile ($R^1$, $R^2$=isobutyl; Ber. 14 (1881), 1867–1870), α-iminodi-(phenylpropionitrile) ($R^1$, $R^2$=benzyl; Annalen, 219 (1883), 186–194) and, if hexamethylenetetramine is used instead of the aldehyde/ammonia, unsubstituted iminodiacetonitrile ($R^1$, $R^2$=hydrogen; Annalen, 278 (1894), 229–233). In all these publications, only symmetric dinitrile compounds are described.

M. Bejaud et al. (Bull. Soc. Chem. France 1976, pages 1425–1430) were able to show that, in the acetaldehyde/hydrocyanic acid/methylamine (or ammonia) system, there are very complex equilibria between acetaldehyde/cyanohydrin, α-aminopropionitrile (or the N-methyl compound) and α-iminodipropionitrile (or the N-methyl compound) on the one hand and between these compounds and the particular starting materials used to prepare them on the other hand. Because of the ease with which these equilibria could be established, it was not to be expected that it would be possible to prepare asymmetric dinitriles I ($R^1$, $R^2$) by selective condensation of an aminonitrile III with an aldehyde-cyanohydrin II. The stated publication describes only the preparation of the two symmetric α-imino- and α-methyliminodipropionitriles.

Another publication (J. prakt. Chem. 89 (1914), 361–371) describes the preparation of α-iminodinitriles starting from the corresponding α-aminonitriles, by converting these to the hydrochloride salts, decomposing these salts with KOH, dissolving the resulting purified α-aminonitriles in ether, drying the solution, distilling off the ether and condensing the product. Condensation was achieved, for example, in the course of one month at room temperature.

Japanese Published Application No. 21,070/63 describes the preparation of α-iminodiacetonitrile and symmetric α-iminodiacetonitriles which are alkyl-substituted in the α-position, by reacting the corresponding α-aminonitriles with a carbonyl compound in a first stage and then, in a second stage, treating the resulting reaction mixture with hydrocyanic acid. In the first stage, a water/alcohol mixture is used as the reaction medium.

German Laid-Open Application DOS No. 1,493,752 points out that α-iminodipropionitrile is obtained as a by-product in the preparation of 2-aminopropionitrile from hydrocyanic acid, ammonia and acetaldehyde. In the distillation of the end product 2-aminopropionitrile, ammonia is eliminated and the symmetric dinitrile is formed. The laid-open application describes a two-stage process in which acetaldehyde is reacted with HCN and anhydrous NH3 to give α-iminodipropionitrile, and the intermediate is dried and then, in a second stage, converted with NH3 to the aminonitriles. Additional solvents are not used, as shown by Example 5, which describes a reaction of 2-aminopropionitrile with lactonitrile in the course of more than 12 hours.

We have found the novel α-iminoacetonitriles of the formula I

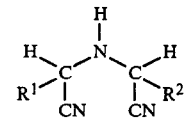

where the individual radicals $R^1$ and $R^2$ can be identical or different and are each hydrogen, an aliphatic, cycloaliphatic, araliphatic or aromatic radical, and, if $R^1$ and $R^2$ are identical, they are each an araliphatic, cycloaliphatic or aromatic radical or ethyl, methoxymethyl, ethoxymethyl or hept-3-yl, or, if $R^1$ and $R^2$ are identical and are each aralkyl, then they are each aralkyl of more than 7 carbon atoms.

Furthermore, we have found that asymmetric α-iminodiacetonitriles of the formula I

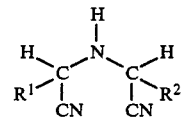

where the individual radicals $R^1$ and $R^2$ are different and are each hydrogen or an aliphatic, cycloaliphatic, araliphatic or aromatic radical, are advantageously obtained by reacting an aldehyde-cyanohydrin with an aminonitrile if an aldehyde-cyanohydrin of the formula II

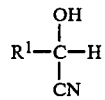

where $R^1$ has the above meanings, is reacted with an aminonitrile of the formula III

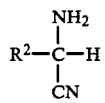

where $R^2$ has the above meanings but differs from $R^1$.

Furthermore, we have found that symmetric α-iminodiacetonitriles of the formula I

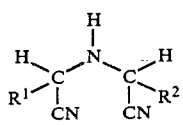   I where the individual radicals $R^1$ and $R^2$ are identical and are each a cycloaliphatic, araliphatic or aromatic radical or ethyl, methoxymethyl, ethoxymethyl or hept-3-yl, and, if $R^1$ and $R^2$ are each aralkyl, then they are each aralkyl of more than 7 carbon atoms, are advantageously obtained by reacting an aldehyde-cyanohydrin with an aminonitrile if an aldehyde-cyanohydrin of the formula II

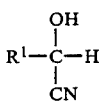   II where $R^1$ has the above meanings, is reacted with an aminonitrile of the formula III

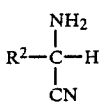   III where $R^2$ has the above meanings, in the presence of a lower alkanol, using from 5 to 95% by weight, based on the amount of lower alkanol, of starting material III.

Furthermore, we have found that α-iminodiacetonitriles of the formula I

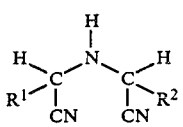   I where the individual radicals $R^1$ and $R^2$ can be identical or different and are each hydrogen or an aliphatic, cycloaliphatic, araliphatic or aromatic radical and, if $R^1$ and $R^2$ are identical, they are each an araliphatic, cycloaliphatic or aromatic radical or ethyl, methoxymethyl, ethoxymethyl or hept-3-yl, or, if $R^1$ and $R^2$ are identical and are each aralkyl, then they are each aralkyl of more than 7 carbon atoms, are advantageously obtained by converting an aminonitrile if the haloacetonitrile of the formula IV

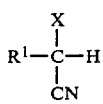   IV where $R^1$ has the above meanings and X is halogen, is reacted with an aminonitrile of the formula III

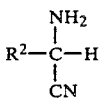   III where $R^2$ has the above meanings, in the presence of an auxiliary base.

Where acetaldehyde-cyanohydrin or α-bromo-α-phenylacetonitrile and α-aminoacetonitrile are used, the reaction can be represented by the following equations:

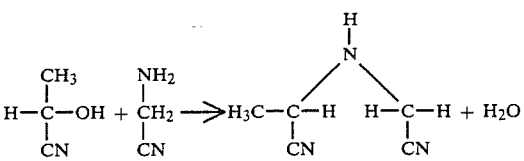

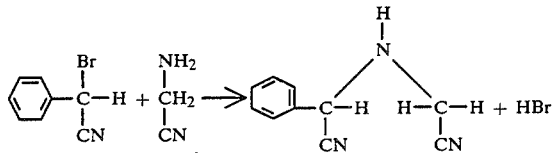

Compared with the conventional processes, the process according to the invention gives α-iminodiacetonitriles in better space-time yield and generally in better yield and purity, by a simpler and more economical route. In view of the prior art, all these advantageous properties are surprising. On the basis of the publication by Bejaud (loc. cit.), it was to be expected that only the formation of symmetric end products would take place or, in the most advantageous case, a mixture of heterogeneous end products would be formed, the number of these being large owing to the complex equilibrium conditions and the mixture containing α-iminodiacetonitriles I only as by-products. It is also surprising that particularly the stable aminonitriles III, instead of undergoing autocondensation, give a high selective yield of end product I. It was also not to be supposed that haloacetonitriles would react with the starting materials III to give in particular asymmetric end products I in good yields, instead of heterogeneous mixtures.

Moreover, it was surprising that, in the preparation of symmetric end products, the amounts of solvent according to the invention give high yields, although the examples of Japanese Published Application No. 21,070/63 show that the reaction in aqueous solutions containing a very small amount of alcohol gives yields of only 40–45%. On the other hand, Example 5 of German Laid-Open Application DOS No. 1,493,752 describes the preparation of α-iminodipropionitrile in the absence of additional solvent (or only in the presence of the water of reaction formed) and with high yields. It is also surprising that, as starting materials III, it is possible to use water-containing crude aminonitriles, for example the unpurified reaction product from an aminonitrile synthesis, without any significant hydrolysis of end product I occurring.

Table 1 shows rates of conversion of aminonitriles III to α-iminodiacetonitriles in which $R^1$ and $R^2$ are identical and have the above meanings. Solutions of aminonitriles in the stated concentration are kept at 22° C. for the stated conversion time. The conversion is monitored by analyzing the content (all data in g). As shown in Table 1, the most stable aliphatic aminonitriles are those having the higher aliphatic radical. However, this Table also shows that, in the presence of water or, in particular, methanol, there is a high tendency to undergo autocondensation. The high selectivity of the novel preparation of asymmetric end products even in the presence of these solvents is therefore surprising.

TABLE 1

| Time (hours) | $R^1,R^2$ = H Content | $H_2O$ | $R^1,R^2$ = $CH_3$ Content | $H_2O$ | $R^1,R^2$ = $CH_3$ Content | $H_2O$ | $R^1,R^2$ = $CH_3$ Content | MeOH | $R^1,R^2$ = $C_2H_5$ Content | $H_2O$ |
|---|---|---|---|---|---|---|---|---|---|---|
| 0 | 97.6 | 2.4 | 100 | 0 | 80 | 20 | 25 | 75 | 98 | 2 |
| 8 | | | | | 68 | | | | | |
| 24 | 95.3 | | 90 | | | | 19 | | 94 | |
| 144 | 90.5 | | 69 | | | | 13 | | 75 | |

The starting materials II, III and IV can be reacted in stoichiometric amounts, or one or other of the components can be used in excess; advantageously from 1 to 2, preferably from 1 to 1.2, moles of aldehyde-cyanohydrin II or from 1 to 1.5, preferably from 1 to 1.2, moles of haloacetonitrile IV are employed per mole of aminonitrile III. Preferred starting materials II, III and IV, and accordingly preferred end products I, are those of the formulae where $R^1$ and $R^2$ can be identical or different and are each hydrogen or alkyl of 1 to 20, preferably 1 to 8, in particular 1 to 4, carbon atoms which is unsubstituted or substituted by alkoxy and/or alkylthio, each advantageously of 1 to 4 carbon atoms, halogen, preferably chlorine or fluorine, carboxamido or cyano, in particular by one of these groups or atoms, or are each alkenyl of 2 to 20, preferably 2 to 8, in particular 2 to 4, carbon atoms, cycloalkyl of 5 to 8 carbon atoms, aralkyl or alkylaryl of 7 to 12 carbon atoms or phenyl, and X is chlorine or, in particular, bromine. The above radicals can be further substituted by groups or atoms which are inert under the reaction conditions, eg. alkyl, alkoxy or alkylthio, each of 1 to 4 carbon atoms, or by carbalkoxy of 2 to 6 carbon atoms.

Examples of suitable starting materials II are the cyanohydrin of formaldehyde, acetaldehyde, propionaldehyde, n-butyraldehyde, isobutyraldehyde, 2-methylbutyraldehyde, 2-ethylcaproaldehyde, n-valeraldehyde, isovaleraldehyde, 2,2-dimethylpropionaldehyde, n-caproaldehyde, isocaproaldehyde, 2-methylvaleraldehyde, 3-methylvaleraldehyde, 2-ethylbutyraldehyde, 2,2-dimethylbutyraldehyde, 2,3-dimethylbutyraldehyde, 3,3-dimethylbutyraldehyde, enanthaldehyde, 2-methylcaproaldehyde, 3-methylcaproaldehyde, 4-methylcaproaldehyde, 5-methylcaproaldehyde, 2-ethylvaleraldehyde, 2,2-dimethylvaleraldehyde, 3-ethylvaleraldehyde, 2,3-dimethylvaleraldehyde, 4-ethylvaleraldehyde, 4,4-dimethylvaleraldehyde, 3,4-dimethylvaleraldehyde, 2,4-dimethylvaleraldehyde, 2-ethyl-2-methylbutyraldehyde, 2-ethyl-3-methylbutyraldehyde, cyclohexylaldehyde, benzaldehyde and phenylacetaldehyde.

Examples of suitable starting materials III are unsubstituted 2-aminoacetonitrile or 2-aminoacetonitriles which are substituted in the 2-position by methyl, ethyl, n-propyl, isopropyl, n-butyl, isobutyl, sec.-butyl, cyclohexyl, benzyl or phenyl.

Examples of suitable starting materials IV are unsubstituted 2-chloroacetonitrile and 2-chloroacetonitriles which are substituted in the 2-position by methyl, ethyl, n-propyl, isopropyl, n-butyl, isobutyl, sec.-butyl, cyclohexyl, benzyl or phenyl, as well as the corresponding 2-bromoacetonitriles.

The reaction is advantageously carried out at from 0° to 100° C., preferably from 20° to 60° C., under a reduced or superatmospheric pressure, or preferably under atmospheric pressure, either batchwise or continuously. The reaction of starting materials II and III takes place in the presence of the water of reaction which is formed; although this water of reaction can be separated off continuously during the reaction, it is advantageous and more economical to remove it only during the working up. If required, additional water may also be present during the reaction in order to accelerate it. It is also possible, and is economical, to use crude starting materials which may contain water, as obtained, for example, in the preparation of the starting materials. For example, the aldehyde-cyanohydrin II can be prepared by reacting hydrocyanic acid with an aldehyde, and the reaction mixture can be used directly for the reaction mixture according to the invention. Likewise, for example, the aminonitrile III can be prepared by reacting starting material II with $NH_3$ and can be isolated from the reaction mixture merely by stripping off the excess $NH_3$; in such cases, the starting material III used in the starting mixture according to the invention contains water. In general, from 1 to 2 moles of total water per mole of starting material II can be present in the reaction mixture. Advantageously, the amount of auxiliary base is sufficient completely to bind the HCl formed in the reaction of starting material IV with starting material III.

In the presence or absence of water, the preparation of asymmetric end products I from starting materials II and starting materials III can also be carried out using a lower alkanol to accelerate the reaction; advantageously, from 5 to 95, in particular from 25 to 75, % by weight, based on the lower alkanol, of starting material III is used. In the preparation of symmetric end products I from starting material II and starting material III, lower alkanols are used in the above amounts. Expedient lower alkanols are those of 1 to 6 carbon atoms, advantageously ethanol, propanol, isopropanol, n-butanol, isobutanol, sec.-butanol, tert.-butanol and in particular methanol.

The reaction can be carried out as follows: a mixture of starting materials II and III or III and IV, in the presence or absence of water and/or an alkanol, advantageously in the above amounts, is kept at the reaction temperature for the reaction time, advantageously for from 8 to 100 hours. The end product is then isolated from the reaction mixture in a conventional manner, for example by distillation or by removing the water. The end product is as a rule then sufficiently pure to be directly processed further. For example, it is necessary only to distil off the water of reaction under reduced pressure. The most common impurities are unreacted aminonitriles or cyanohydrins, and these can be removed completely or partially by extraction or distillation (thin-film evaporation being a particularly mild method) or, where they are sufficiently water-soluble, by a water wash. However, aminonitrile III and dinitrile I can also be precipitated in an anhydrous solvent, for example as the hydrochlorides, and both salts treated with water. As a result, the dinitrile salt undergoes hydrolytic cleavage, while the more strongly basic aminonitrile III can be separated off as a water-soluble salt.

The reaction of starting material IV and starting material III is preferred particularly for the preparation of asymmetric end products I which contain an aromatic radical $R^1$. The auxiliary bases used are generally tertiary amines, but it is also possible to employ other bases, for example inorganic bases, such as alkali metal hydroxides or carbonates.

The reaction is advantageously carried out in the presence of from 1 to 2, preferably from 1.05 to 1.2, equivalents of the tertiary amine per mole of starting material IV. Advantageous tertiary amines are those of the formula VI

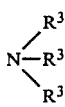
                        VI where the individual radicals $R^3$ can be identical or different and are each a cycloaliphatic, araliphatic, aromatic or, in particular, aliphatic radical, advantageously alkyl of 1 to 6 carbon atoms, or two of the radicals $R^3$ or all of them together with the adjacent nitrogen atom may furthermore be members of a heterocyclic radical, in particular of a 5-membered or 6-membered heterocyclic ring. examples of suitable amines are trimethylamine, triethylamine, tripropylamine, triisopropylamine, tributylamine, triisobutylamine, tri-sec.-butylamine, tri-tert.-butylamine, triamylamine, N,N-dimethylaniline, N,N-dimethyltoluidine, N-methylpiperidine, N-methylpyrrolidine, N-methylmorpholine and pyridine. Triethylamine and trimethylamine are preferred.

It is also expedient to use organic solvents, advantageously non-polar ones, in the reaction of starting materials IV, eg. ethers, such as ethyl propyl ether, methyl tert.-butyl ether, n-butyl ethyl ether, di-n-butyl ether, diisobutyl ether, diisoamyl ether, diisopropyl ether, cyclohexyl methyl ether, diethyl ether, ethylene glycol dimethyl ether, tetrahydrofuran or dioxane, or mixtures of these; diisopropyl ether is preferred. Advantageously, the solvent is used in an amount of from 50 to 10,000, preferably from 400 to 1,000, % by weight, based on starting material IV.

If required, phase transfer catalysts, eg. fatty alkylammonium halides, can also be used in the reaction of starting material IV.

The α-iminodiacetonitriles obtainable by the process of the invention are useful starting materials for the preparation of dyes, fungicides, bactericides, herbicides, textile assistants, anticorrosion agents, complex-forming agents in electroplating baths and inhibitors for antifreezes. Regarding the use of these compounds, reference may be made to the above publications.

In a preferred form for use, the end products I thus obtained are converted, by the procedures described in U.S. patent application Ser. No. 547,852 and Ser. No. 547,853, initially to 2-aminopyrazines of the formula Ia

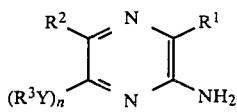
                        Ia by reaction with
(1a) a hydrogen halide of the formula XI

H—X                                    XI or (1b) an alcohol and/or a thioalcohol of the formula VII $HYR^3$                                 VII and a hydrogen halide of the formula XI

H—X                                    XI or (1c) an alcohol and/or a thioalcohol of the formula VII $HYR^3$                                 VII in the presence of an alkali metal compound and/or an alkaline earth metal compound.

$R^1$, $R^2$ and X have the above general and preferred meanings, $R^3$ has the general and preferred meanings of $R^1$ and $R^2$, but is not hydrogen, Y is oxygen or sulfur and n is 0 or, if reaction (1c) is carried out, may be 1. The substances can be reacted in stoichiometric amounts, or an excess of one or other of the components can be used; preferably from 1.5 to 6, in particular from 2 to 5, moles of starting material XI are employed per mole of substance I in the case of process (1a), from 1.5 to 6, in particular from 2 to 5, moles of starting material XI and/or from 0.1 to 10, in particular from 0.5 to 3, moles of starting material VII are employed per mole of substance I in the case of process (1b), and from 5 to 50, in particular from 10 to 25, % by weight, based on substance VII, of substance I is employed in the case of process (1c). The reactions (1a), (1b) and (1c) are advantageously carried out at from 0° to 100° C., advantageously at from 40° to 80° C. in the case of reaction (1a), advantageously at from 20° to 80° C., preferably from 30° to 70° C., in the case of reaction (1b) and advantageously at from 0° to 80° C., preferably from 20° to 60° C., in the case of reaction (1c), under reduced, atmospheric or superatmospheric pressure, either batchwise or continuously. The reaction time is advantageously from 0.1 to 200, preferably from 3 to 48, hours. If required, organic solvents which are inert under the reaction conditions may be used. Examples of suitable solvents are aromatic, aliphatic and cycloaliphatic hydrocarbons, halohydrocabons, in particular chlorohydrocarbons, ethers and mercaptans. Advantageously, the solvent is used in an amount of from 40 to 10,000, preferably from 50 to 1,500, percent by weight, based on substance I. If appropriate, starting material VII itself can also be used as the solvent.

Reaction (1c) is carried out in the presence of an alkaline earth metal compound or, in particular, an alkali metal compound, advantageously in catalytic amounts; expediently, from 0.1 to 2, preferably from 0.2 to 0.6, equivalents of base are employed per mole of substance I. Alcoholates, mercaptides, hydroxides or cyanides, or mixtures of these, are advantageously used.

The resulting substances Ia, in pure or crude form, are preferably converted to 2-halo- or 2-cyanopyrazines of the formula

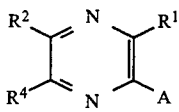   Ic by reaction at from −50° to +50° C. with (2a) an alkali metal nitrite or an alkyl nitrite in the presence of water and/or an organic solvent and (2a1) with tetrafluoboric acid or (2a2) a hydrohalic acid of the formula

   XI in the form of a 10–80 percent strength by weight solution, using from 1 to 5 moles of starting material XI per mole of substance Ia, or (2b) a nitrosyl halide in the presence of an organic solvent which is inert under the reaction conditions, and, if desired, by reaction of the resulting 2-halopyrazines of the formula

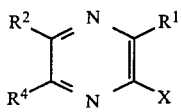   VIII with copper cyanide and, if required, an alkali metal cyanide and/or an alkaline earth metal cyanide at from 80° to 200° C. $R^1$, $R^2$, $R^3$, Y and X have the above general and preferred meanings, A is halogen, preferably chlorine, bromine or fluorine, or cyano, and $R^4$ is hydrogen or a radical $R^3Y$.

Preferred starting materials XI are hydrochloric acid and hydrobromic acid. The nitrosyl halides used are those of the formula

   IX

Preferred alkali metal nitrites are sodium nitrite and potassium nitrite, and preferred alkyl nitrites are those of the formula

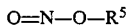   X where $R^5$ is alkyl of 1 to 6 carbon atoms, advantageously amyl nitrite, ethyl nitrite or neopentyl nitrite. Process (2a1) (tetrafluoboric acid) is advantageously carried out using an organic solvent or, preferably, a mixture of an organic solvent with additional water. Process (2a2) can be carried out using an organic solvent, if appropriate mixed with additional water, but is advantageously carried out in an aqueous medium.

Instead of the starting materials IX, it is also possible to use the reaction mixture from their preparation, for example from NO and halogen, in particular bromine. The starting materials can be reacted in stoichiometric amounts, or an excess of one or other of the components can be used; preferably from 1 to 3, in particular from 1.05 to 1.2, moles of alkali metal nitrite or alkyl nitrite, preferably from 1 to 3, in particular from 1.05 to 1.2, moles of $HBF_4$ or from 1 to 3, in particular from 1.05 to 1.5, moles of starting material IX are employed per mole of substance Ia. From 1 to 5, preferably from 2 to 4, moles of starting material XI are used per mole of substance Ia. Reaction (2a) or (2b) is carried out at from −50° to +50° C., advantageously at from −30° to +40° C., in particular from −20° to +25° C., in the case of process (2a) and advantageously from −25° to +40° C., in particular from −25° to 0° C., in the case of process (2b), under reduced, atmospheric or superatmospheric pressure, either batchwise or continuously. Processes (2a) and (2b) are carried out using solvents. Water is introduced into the reaction wholly or partly in the form of solutions of the acids XI and advantageously in the form of solutions of the alkali metal nitrite. Depending on whether process (2a) or process (2b) is being carried out, suitable organic solvents are in general halohydrocarbons (preferably for (2b)), in particular chlorohydrocarbons; ethers (preferably for (2a)), alkanols and cycloalkanols (preferably for (2a)), sulfoxides and sulfones, esters (preferably used in the absence of additional amounts of water), carboxylic acids of 2 to 6 carbon atoms (preferably for (2a)), and mixtures of these. Advantageously, the organic solvent and/or additional water (not including water of reaction) are used in an amount of from 50 to 5,000, preferably 100 to 1,000, percent by weight, based on substance Ia.

Some or all of the solvent may also be employed in the form of the corresponding solution of the starting materials, for example of tetrafluoboric acid. Starting material XI is used in the form of a 10–80, preferably 30–70, percent strength by weight solution. The reaction time is advantageously from 0.2 to 5 hours. In a preferred embodiment, nitrosyl bromide is employed in a single-vessel process. First, bromine in a suitable solvent, for example one of those mentioned above, is initially taken, and is converted to NOBr by passing in NO at from +10° to −40° C., preferably from −10° to −20° C., and the product is then metered, at this temperature, into a solution of the 2-aminopyrazine Ia in one of the above solvents.

Substance VIII can be reacted with copper cyanide alone, in stoichiometric amounts or expediently in excess; advantageously, from 1 to 2, preferably from 1.05 to 1.5, moles of copper cyanide are used per mole of starting material VIII. Some of the copper cyanide can be replaced with an alkali metal cyanide and/or an alkaline earth metal cyanide, advantageously lithium cyanide, calcium cyanide, barium cyanide or preferably sodium cyanide or potassium cyanide; advantageously from 1 to 3, preferably from 1.1 to 1.5, moles of alkali metal cyanide and/or alkaline earth metal cyanide are employed per mole of starting material VIII. Mixtures containing from 10 to 50, preferably from 15 to 25, mole %, based on all cyanides, of copper cyanide are advantageous. The reaction is carried out at from 80° to 200° C., preferably from 120° to 160° C., under reduced, atmospheric or superatmospheric pressure, either continuously or batchwise. It is expedient to use a heterocyclic solvent which is inert under the reaction conditions, advantageously in an amount of from 100 to 5,000, preferably from 200 to 1,000, percent by weight, based on substance Ia. The reaction time is from 1 to 12 hours.

As a result of this elegant 3-stage procedure (III→I→Ia→Ic) a large number of synthesis routes in the abovementioned industrial fields, for example for folic acid compounds, surprisingly became possible or became more economical and simpler.

EXAMPLES 1–19

Molar amounts of cyanohydrin II and aminonitrile III were reacted under the conditions stated in Tables 1 and 3. The course of the reaction was monitored potentiometrically (conversion of the aminonitrile III) and by thin-layer chromatography. When the conversion remained constant, the water of reaction and, where relevant, the solvent were distilled off under reduced pressure at the reaction temperature (working up I). The residue which remained after the solvent had been removed could be distilled (working up Ia). In the case of relatively large amounts of reaction mixture, water was removed by a two-stage procedure in a thin-film evaporator under reduced pressure at from 20° to 200° C. during a residence time of from 0.1 to 10 minutes (working up II); if required, the mixture was also distilled (IIa). The structure was confirmed by elemental analyses and $H^1$-NMR and $C^{13}$-NMR analyses. The purity was monitored by means of thin-layer chromatography in conjunction with potentiometric titration of the unreacted aminonitrile and determination of cyanohydrin by the Liebig method. Details are given in Tables 2, 2a and 3. The compositions of the reaction mixtures are stated in % by weight in Table 2a.

TABLE 2

(Preparation of asymmetric α-iminodiacetonitriles)

| Example | Cyanohydrin $R^1$ | Amount in g | Aminonitrile $R^2$ | Amount in g | $H_2O$ (g) | Temperature (°C.) | Time (d) | Methanol (g) | Conversion (%) | Selectivity (%) |
|---|---|---|---|---|---|---|---|---|---|---|
| 1 | $CH_3$ | 142 | H | 112 | 3 | 40 | 1 | 257 | 95 | 97 |
| 1a | $CH_3$ | 284 | H | 224 | 27 | 40 | 1 | — | 97 | 99 |
| 2 | $C_2H_5$ | 255 | H | 168 | 5 | 25 | 3 | — | 94 | 97 |
| 3 | i-$C_3H_7$ | 198 | H | 112 | 3 | 25 | 3 | — | 93 | 95.4 |
| 4 | i-$C_4H_9$ | 452 | H | 224 | 7 | 25 | 3 | — | 91 | 98 |
| 4a | i-$C_4H_9$ | 452 | H | 224 | 27 | 50 | 0.4 | — | 96 | 99 |
| 5 | $MeOCH_2$ | 10.1 | H | 5.6 | — | 50 | 3 | 17 | 92 | 94 |
| 6 | $CH_3$ | 284 | $C_2H_5$ | 336 | 17 | 25 | 2 | — | 96 | 88 |
| 7 | $CH_3$ | 284 | i-$C_3H_7$ | 392 | 55 | 40 | 2.5 | — | 92 | 93 |
| 8 | $CH_3$ | 7 | $CH_3SCH_2CH_2$ | 13 | 0.2 | 40 | 3 | — | 93 | 94 |
| 9 | $CH_3$ | 71 | $CH_3OCH_2$ | 100 | 2.4 | 40 | 2.5 | 185 | 94.5 | 94 |
| 10 | $CH_3$ | 35.5 | $C_2H_5OCH_2$ | 57 | 0.3 | 40 | 4 | — | 94.5 | 96 |
| 11 | $CH_3$ | 142 | $C_2H_5$—CH—$C_4H_9$ | 308 | 3 | 40 | 1 | — | 97 | 95 |
| 12 | $CH_3$ | 57 | $C_7H_7$ | 117 | 1 | 50 | 3 | — | 96 | 93 |
| 13 | $MeOCH_2$ | 10.1 | $C_2H_5OCH_2$ | 11.4 | — | 50 | 3 | 23 | 95 | 90 |
| 14 | $MeOCH_2$ | 20.2 | i-$C_3H_7$ | 19.6 | 3 | 50 | 4 | 47 | 94.5 | 87 |
| 15 | $CH_3$ | 14 | $C_6H_5$ | 26.4 | — | 40 | 4 | — | 90 | 75 |

TABLE 2a (Quality of the asymmetrically substituted α-iminodiacetonitriles; data in % by weight)

(1)

$$R^1-\underset{CN}{\underset{|}{CH}}\diagup\underset{N}{\overset{H}{|}}\diagdown\underset{CN}{\underset{|}{CH}}-R^1$$

(2)

$$R^2-\underset{CN}{\underset{|}{CH}}\diagup\underset{N}{\overset{H}{|}}\diagdown\underset{CN}{\underset{|}{CH}}-R^2$$

(3)

$$H_5C_6-\underset{CN}{\underset{|}{CH}}\diagup\underset{N}{\overset{CH_2-C_6H_5}{|}}\diagdown\underset{CN}{\underset{|}{CH}}-C_6H_5$$

| Example | Worked up by process | End product I | Starting material III | Starting material II | By-product (1) | By-product (2) | By-product (3) | $n_D^{20}$ (Fp) |
|---|---|---|---|---|---|---|---|---|
| 1 | IIa | 94 | 1.3 | 1.7 | 1.5 | 1.5 | | 1.4511 |
| 1a | II | 97.8 | 1.0 | 1.0 | trace | trace | | 1.4492 |
| 2 | I | 90 | 1.1 | | | | | |
| | Ia | 95 | 0.8 | | 1 | 1 | | 1.4506 |
| 3 | I | 92 | 2.5 | | 1 | 0.5 | | |
| 4 | I | 92 | 2.7 | | 1 | 1 | | |
| 4a | II | 95.5 | 2 | 0.5 | 1 | 1 | | 1.4530 |
| 5 | I | 90 | 1.9 | | | 3 | | |
| 6 | II | 92 | 1.1 | 1.9 | 3 | 2 | | 1.4455 |
| 7 | I | 92 | 5 | | 2 | 1 | | |
| 8 | I | 89 | 2.6 | | 3 | | | |
| 9 | IIa | 94 | 4 | | 2 | | | 1.4492 |
| 10 | I | 94 | 3 | | | 1 | | |
| 11 | II | 92 | 3 | | 2 | 3 | | |
| 12 | I | 90 | 3 | | 5 | 2 | | (M.p. 40° C.) |
| 13 | I | 87 | 3 | | 3 | 7 | | |
| 14 | I | 84.5 | 2.5 | | 10 | 3 | | |
| 15 | I | 74 | 4 | | 17 | (5) | | |

TABLE 3

(Novel symmetrically substituted α-iminodiacetonitriles I)

| Example | $R^1=R^2$ | Cyanohydrin II g | Aminonitrile III g | $H_2O$ g | Temperature (°C.) | Time (days) | Methanol g | Conversion (%)[2] | Selectivity[3] (%) | Purity[1] % by weight |
|---|---|---|---|---|---|---|---|---|---|---|
| 16 | $C_2H_5$— | 25.5 | 25.2 | 0.5 | 40 | 2 | — | 96.3 | 100 | 95 |
| 17 | n-$C_4H_9$—CH— with $C_2H_5$ | 77.5 | 77 | 0.7 | 60 | 3 | — | 95.5 | 96 | 93 |

TABLE 3-continued (Novel symmetrically substituted α-iminodiacetonitriles I)

| | | Aminonitrile III | | | | | | | Selec- | Purity[1] |
| | | Cyanohydrin II | | H$_2$O | Temperature | Time | Methanol | Conversion | tivity[3] | % by |
| Example | R$^1$=R$^2$ | g | g | g | (°C.) | (days) | g | (%)[2] | (%) | weight |
|---|---|---|---|---|---|---|---|---|---|---|
| 18 | CH$_3$—OCH$_2$— | 101 | 100 | — | 50 | 2 | 206 | 97 | 98 | 95 |
| 19 | C$_2$H$_5$—OCH$_2$— | 57.5 | 57 | — | 50 | 3 | 123 | 95 | 93 | 90 |

[1] after drying
[2] based on aminonitrile III used
[3] based on aminonitrile III converted

EXAMPLES 20–22

Molar amounts of 2-bromophenylacetonitrile (196 g) and aminonitrile III were dissolved in 800 g of diisopropyl ether, and 1 mole (101 g) of triethylamine was added dropwise in the course of 4 hours at 22° C. A semicrystalline precipitate formed immediately, and this was converted in the reaction mixture after 48 hours to a well crystallized salt by the addition of 170 g of acetonitrile. After a further 24 hours, the salt was filtered off and was washed with 200 g of a diisopropyl ether/acetonitrile mixture of the above weight ratio. The dry salt contained 95% by weight of the theoretical amount of Br$^\ominus$. The mother liquor and the wash liquid were combined, washed with water and then evaporated down under reduced pressure at from 25° to 40° C. The residue was analyzed by thin-layer chromatography. Details are shown in Table 4.

TABLE 4

(Aryl-substituted α-iminodiacetonitriles I)

| | | Aminonitrile III | End product I | Yield in % of theory, based on |
| Example | R$^2$ | g | g | aminonitrile III used |
|---|---|---|---|---|
| 20 | CH$_3$ | 14 | 142 | 77 |
| 21 | H | 28 | 135 | 79 |
| 22 | C$_6$H$_5$ | 13.2 | 25 | 55 |

We claim:
1. An α-iminodiacetonitrile of the formula

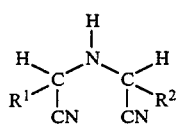

where the individual radicals R$^1$ and R$^2$ are different and each is selected form the group consisting of:
hydrogen;
alkyl of 1 to 20 carbon atoms and said alkyl substituted by alkoxy or alkylthio, each of 1 to 4 carbon atoms, halogen, carboxamido or cyano;
alkenyl of 2 to 20 carbon atoms;
cycloalkyl of 5 to 8 carbon atoms;
aralkyl or alkylaryl of 7 to 12 carbon atoms; and
phenyl.

2. An α-iminodiacetonitrile of the formula

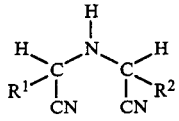

where the individual radicals R$^1$ and R$^2$ are identical and are selected from the group consisting of:
methyl which is substituted by alkoxy or alkylthio, each of 1 to 4 carbon atoms;
cycloalkyl of 5 to 8 carbon atoms; and
phenyl.

3. An α-iminodiacetonitrile as claimed in claim 2 where R$^1$ and R$^2$ represent methyl substituted by alkoxy or alkylthio, each of 1 to 4 carbon atoms.

4. A process for the preparation of an asymmetric α-iminodiacetonitrile of the formula

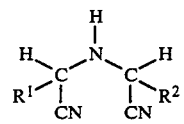

where the individual radicals R$^1$ and R$^2$ are different and each is selected form the group consisting of:
hydrogen;
alkyl of 1 to 20 carbon atoms and said alkyl substituted by alkoxy or alkylthio, each of 1 to 4 carbon atoms, halogen, carboxamido or cyano;
alkenyl of 2 to 20 carbon atoms;
cycloalkyl of 5 to 8 carbon atoms;
aralkyl or alkylaryl of 7 to 12 carbon atoms; and
phenyl,
which process comprises: reacting an aldehyde-cyanohydrin of the formula

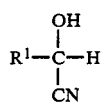

where R$^1$ has the above meanings, with an aminonitrile of the formula

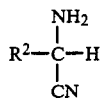

where R$^2$ has the above meanings but differs from R$^1$.

5. A process as claimed in claim 4, wherein the reaction is carried out using from 1 to 2 moles of aldehyde-cyanohydrin II per mole of aminonitrile III.

6. A process as claimed in claim 4, wherein the reaction is carried out at from 0° to 100° C.

7. A process as claimed in claim 4, wherein the reaction is carried out in the presence of a lower alkanol, using from 5 to 95% by weight, based on the lower alkanol, of starting material III.

8. A process for the preparation of a symmetric α-iminodiacetonitrile of the formula

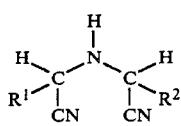

where the individual radicals $R^1$ and $R^2$ are identical and are selected from the group consisting of
methyl which is substituted by alkoxy or alkylthio, each of 1 to 4 carbon atoms;
cycloalkyl of 5 to 8 carbon atoms; and
phenyl,
which process comprises: reacting an aldehyde-cyanohydrin of the formula

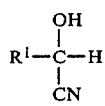

where $R^1$ has the above meanings with an aminonitrile of the formula

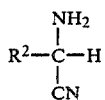

where $R^2$ has the above meanings and is identical to $R^1$, in the presence of a lower alkanol, using from 5 to 95% by weight, based on the amount of lower alkanol, of the starting material III.

9. A process as claimed in claim 8, wherein the reaction is carried out using from 1 to 1.2 moles of aldehyde-cyanohydrin II per mole of aminonitrile III.

10. A process as claimed in claim 8, wherein the reaction is carried out at from 0° to 100° C.

11. A process for the preparation of an α-iminodiacetonitrile of the formula

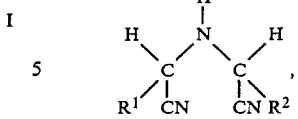

where $R^1$ is phenyl and $R^2$ is selected from the group consisting of
hydrogen,
alkyl of 1 to 20 carbon atoms or said alkyl substituted by alkoxy or alkylthio, each of 1 to 4 carbon atoms, halogen, carboxamido or cyano,
alkenyl of 2 to 20 carbon atoms,
cycloalkyl of 5 to 8 carbon atoms,
aralkyl or alkylaryl of 7 to 12 carbon atoms, and
phenyl,
which process comprises: reacting a haloacetonitrile of the formula

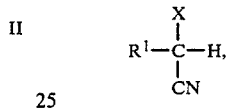

where $R^1$ has the above meanings and X is halogen, with an aminonitrile of the formula

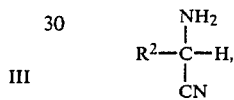

where $R^2$ has the above meanings, in the presence of an auxiliary base selected from the group consisting of
a tertiary amine;
an alkali metal hydroxide and
an alkali metal carbonate, and also in the presence of an organic solvent.

12. A process as claimed in claim 11, wherein the reaction is carried out using from 1 to 1.5 moles of haloacetonitrile IV per mole of aminonitrile III.

13. A process as claimed in claim 11, wherein the reaction is carried out at from 0° to 100° C.

14. A process as claimed in claim 11 wherein $R^2$ is hydrogen, methyl, ethyl, n-propyl, isopropyl, n-butyl, isobutyl, sec.-butyl, cyclohexyl, benzyl or phenyl, and X is bromine or chlorine.

15. A process as claimed in claim 14 wherein $R^2$ is hydrogen and X is bromine.

* * * * *